United States Patent
Acker et al.

(10) Patent No.: US 12,339,201 B2
(45) Date of Patent: Jun. 24, 2025

(54) GAS SENSOR MODULE

(71) Applicant: Mallinckrodt Pharmaceuticals Ireland Limited, Dublin (IE)

(72) Inventors: Jaron Acker, Madison, WI (US); Peter James Clark, Hazelwood, MO (US); Cedric Assambo, Hazelwood, MO (US); Michael McAtamney, Hazelwood, MO (US); John Klaus, Cottage Grove, WI (US); Robin Roehl, Hazelwood, MO (US)

(73) Assignee: Mallinckrodt Pharmaceuticals Ireland Limited, Dublin (IE)

( * ) Notice: Subject to any disclaimer, the term of this patent is extended or adjusted under 35 U.S.C. 154(b) by 553 days.

(21) Appl. No.: 17/299,171

(22) PCT Filed: Dec. 3, 2019

(86) PCT No.: PCT/US2019/064278
§ 371 (c)(1),
(2) Date: Jun. 2, 2021

(87) PCT Pub. No.: WO2020/117836
PCT Pub. Date: Jun. 11, 2020

(65) Prior Publication Data
US 2022/0034764 A1    Feb. 3, 2022

Related U.S. Application Data

(60) Provisional application No. 62/774,687, filed on Dec. 3, 2018.

(51) Int. Cl.
*G01N 1/24* (2006.01)
*A61M 16/04* (2006.01)
(Continued)

(52) U.S. Cl.
CPC ............... *G01N 1/24* (2013.01); *A61M 16/04* (2013.01); *A61M 16/085* (2014.02);
(Continued)

(58) Field of Classification Search
CPC ... G01N 1/24; G01N 33/0009; A61M 16/085; A61M 16/1005; A61M 16/104;
(Continued)

(56) References Cited

U.S. PATENT DOCUMENTS

2007/0167853 A1*   7/2007   Melker ................. A61B 5/411
                                                 600/529
2007/0193333 A1    8/2007   Wobben
(Continued)

FOREIGN PATENT DOCUMENTS

CN    102107037 A    6/2011
CN    107847698 A    3/2018
(Continued)

OTHER PUBLICATIONS

Notice of Reasons for Rejection for Japanese Application No. 2021-528359, mailed on Sep. 27, 2023, 9 pages.
(Continued)

*Primary Examiner* — Helen C Kwok

(57) ABSTRACT

A removable gas sensor module is provided for a therapeutic gas delivery device. The gas sensor module includes a sample chamber which receives a sample gas from the therapeutic gas delivery device. A gas detection unit includes a plurality of sensors operable to measure at least one property of the sample gas. The sensors include two or more of a gas detection sensor, a humidity sensor, a temperature sensor, or a combination thereof. The gas sensor module is self-contained within the therapeutic gas delivery device and swappable with another gas sensor module.

22 Claims, 7 Drawing Sheets

(51) Int. Cl.
*A61M 16/08* (2006.01)
*A61M 16/10* (2006.01)
*G01N 33/00* (2006.01)

(52) U.S. Cl.
CPC ..... *A61M 16/1005* (2014.02); *G01N 33/0009* (2013.01); *A61M 2016/1025* (2013.01); *A61M 2205/3327* (2013.01); *A61M 2205/3368* (2013.01)

(58) Field of Classification Search
CPC .. A61M 2016/1025; A61M 2016/1035; A61M 2205/3327; A61M 2205/3368; A61M 2205/07; A61M 2205/12; A61M 2205/125; A61M 2205/3358
See application file for complete search history.

(56) References Cited

U.S. PATENT DOCUMENTS

| | | | |
|---|---|---|---|
| 2007/0193335 A1 | 8/2007 | Son | |
| 2014/0127081 A1* | 5/2014 | Fine | A61M 16/12 422/198 |
| 2014/0250975 A1 | 9/2014 | Kane | |
| 2015/0273176 A1* | 10/2015 | Acker | A61M 16/0003 128/202.22 |
| 2015/0351690 A1* | 12/2015 | Toth | A61B 5/291 600/391 |
| 2017/0074820 A1 | 3/2017 | DeBlasio | |
| 2017/0160266 A1 | 6/2017 | Son | |
| 2017/0188908 A1* | 7/2017 | Hoss | G01N 27/3274 |
| 2018/0185606 A1* | 7/2018 | Van Schalkwyk | A61M 16/109 |
| 2018/0243527 A1* | 8/2018 | Zapol | A61M 16/12 |
| 2018/0296781 A1 | 10/2018 | Cole et al. | |
| 2021/0038838 A1* | 2/2021 | Acker | A61M 16/00 |
| 2021/0213235 A1* | 7/2021 | Montgomery | A61M 16/04 |

FOREIGN PATENT DOCUMENTS

| | | |
|---|---|---|
| JP | 2012519038 A | 8/2012 |
| JP | 2016523139 A | 8/2016 |
| JP | 2017509432 A | 4/2017 |
| JP | 2018518297 A | 7/2018 |
| JP | 2018118085 A | 8/2018 |
| WO | 2013151447 A1 | 10/2013 |
| WO | 2015153713 A1 | 10/2015 |
| WO | 2016207838 A1 | 12/2016 |
| WO | 2018157172 A1 | 8/2018 |
| WO | 2019070135 A1 | 4/2019 |
| WO | 2019070136 A1 | 4/2019 |

OTHER PUBLICATIONS

Office Action for Brazilian Application No. BR112021010462-3, mailed on Jul. 5, 2023, 5 pages.
Extended European Search Report for Application No. 19893012.5 mailed on Aug. 23, 2022, 6 pages.
Figaro., "Operating Principle-MOS-Type Gas Sensor," Nov. 30, 2018, Retrieved from Internet URL: https://www.figarosensor.com/technicalinfo/principle/mos-type.html, 4 pages.
International Search Report and Written Opinion for Application No. PCT/US2019/64278 mailed on Feb. 18, 2020, 14 pages.
SPECSENSORS., "Analog Sensor Developer Kit—User Manual," Nov. 2016, 4 pages.
Examination Report No. 1 for Australian Patent Application No. 2019391029, mailed on May 30, 2024, 3 pages.
Office Action for Chinese Patent Application No. 2019800799157, dated Sep. 27, 2024, 21 pages.
Search Report for Chinese Patent Application No. 2019800799157, dated Sep. 24, 2024, 2 pages.
Office Action for Canadian Application No. 3,121,782, mailed on Aug. 19, 2024, 5 pages.
Extended European Search Report for Application No. 24218821.7, dated Jan. 20, 2025, 9 Pages.
Office Action for Mexican Patent Application No. MX20210006500, mailed Nov. 22, 2024, 6 pages.
Office Action for Japanese Patent Application No. 2023-220561, mailed on Nov. 21, 2024, 4 pages.
First Office Action for Chinese Patent Application No. 20198079915.7, mailed Sep. 27, 2024, 23 pages.

* cited by examiner

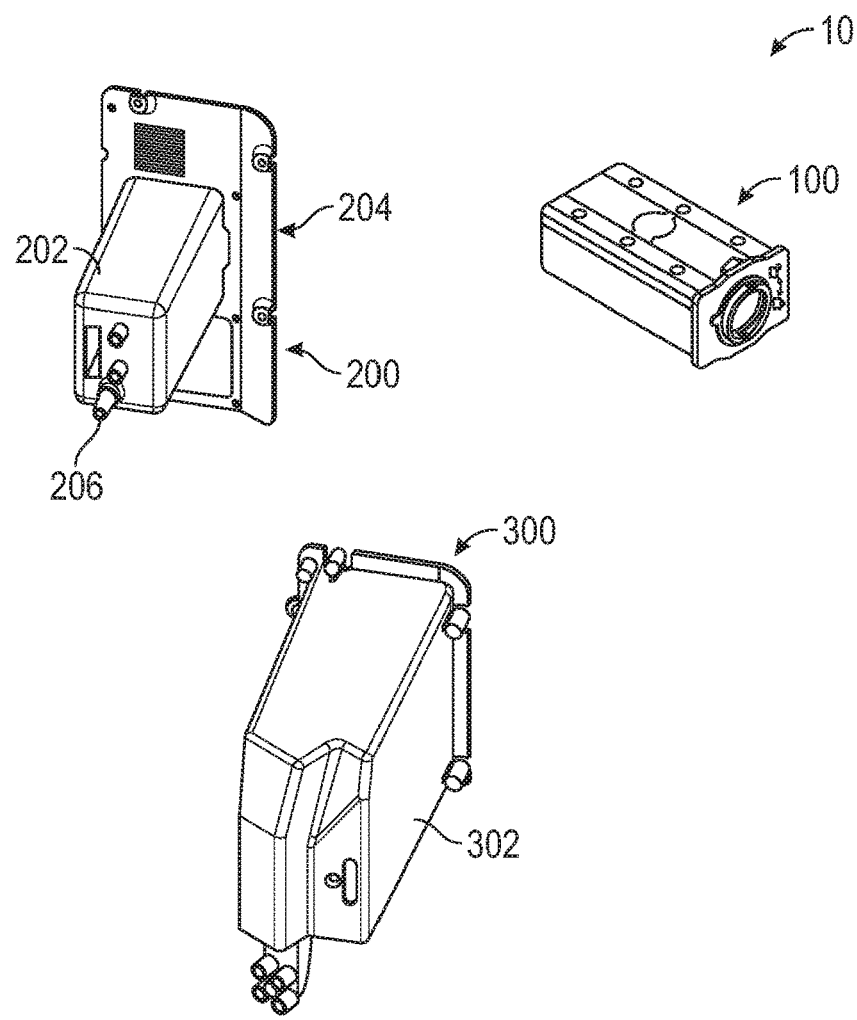
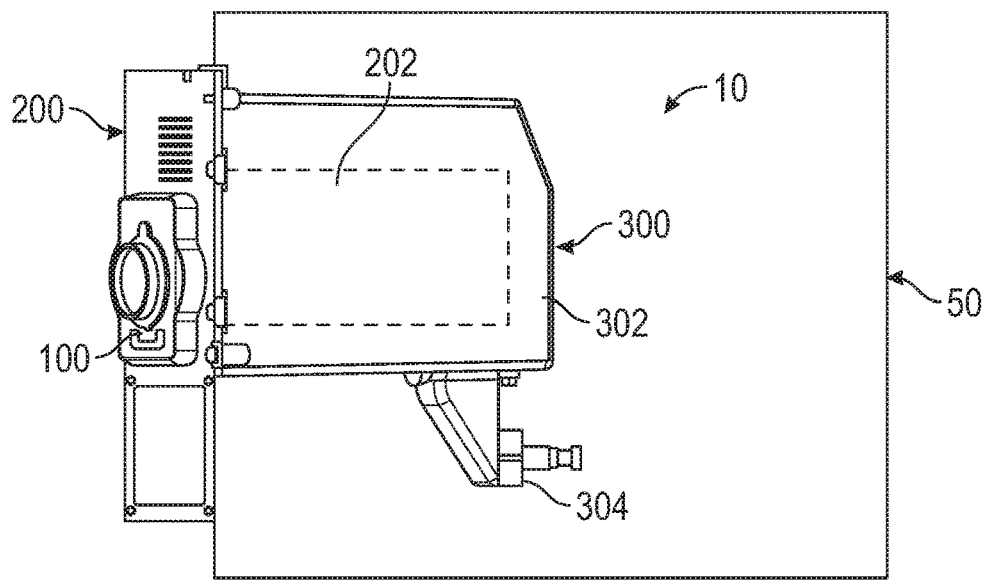
FIG. 1A
FIG. 1B

GAS SENSOR MODULE

CROSS-REFERENCE TO RELATED APPLICATIONS

This application claims the benefit of International Patent Application No. PCT/US2019/064278, filed Dec. 3, 2019, which claims priority to U.S. Provisional Application No. 62/774,687, filed Dec. 3, 2018, the contents of which are entirely incorporated by reference herein.

FIELD

The present disclosure relates generally to gas sensor modules. In one example, the present disclosure relates to gas sensor modules for therapeutic gas delivery devices.

BACKGROUND

Conventionally, a gas detection system needs to be calibrated by the user at intervals detailed in the user manual. For example, high calibration of a gas sampling system may be carried out monthly and may require calibration gas supplies to be available at the facility, as well as a change of sample line connections. During high calibration of the gas sampling system and the change of sample line connections, a gas detection system cannot sample gas. Additionally, incorrect connection of the calibration tubing kit can result in incorrect readings or equipment damage.

BRIEF DESCRIPTION OF THE DRAWINGS

Implementations of the present technology will now be described, by way of example only, with reference to the attached figures, wherein:

FIG. 1A is an exploded view of an exemplary gas sensor assembly according to the present disclosure;

FIG. 1B is an assembled view of the gas sensor assembly of FIG. 1A;

DETAILED DESCRIPTION

Figure 2A:
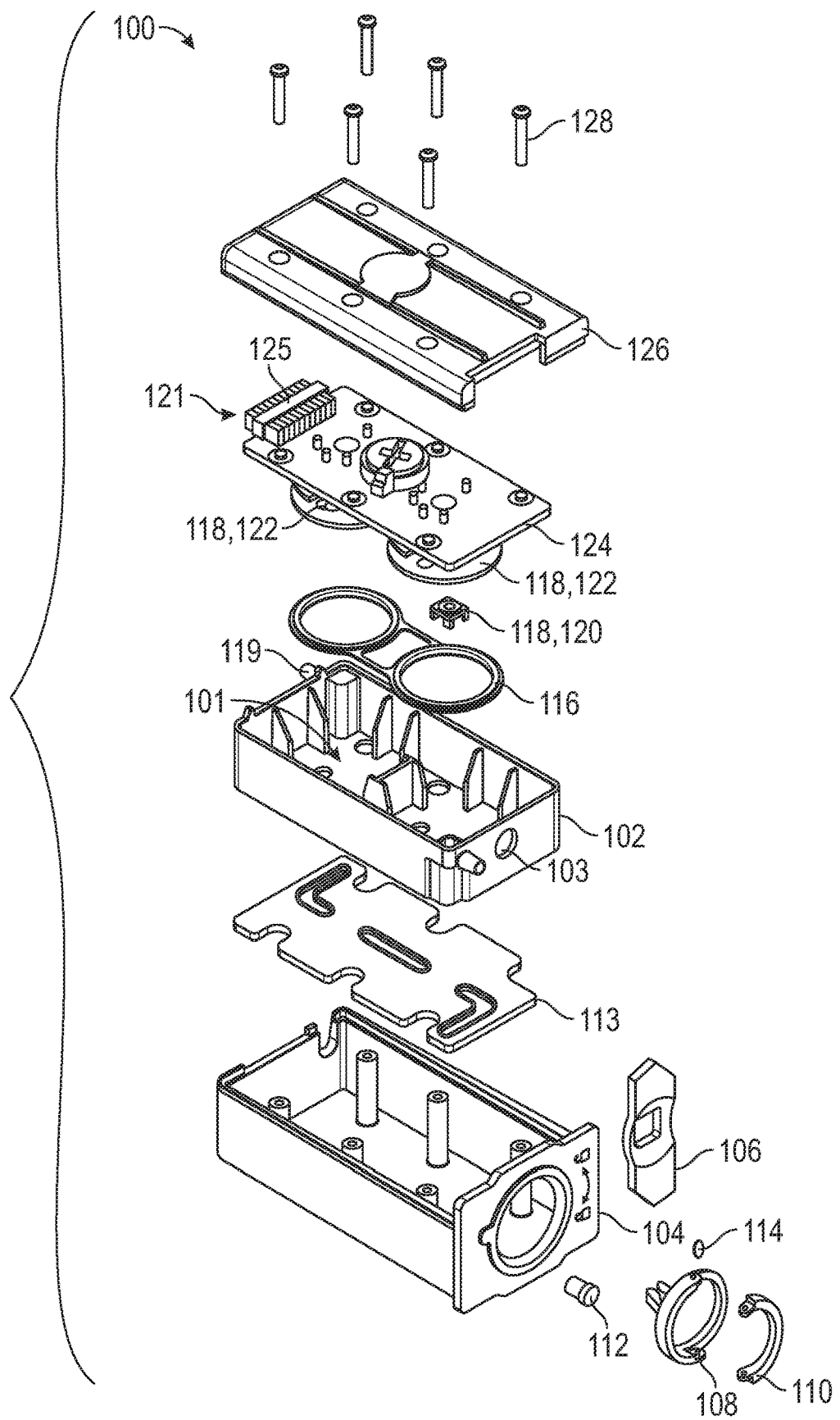
FIG. 2A is an exploded view of an exemplary gas sensor module.

It will be appreciated that for simplicity and clarity of illustration, where appropriate, reference numerals have been repeated among the different figures to indicate corresponding or analogous elements. In addition, numerous specific details are set forth in order to provide a thorough understanding of the examples described herein. However, it will be understood by those of ordinary skill in the art that the examples described herein can be practiced without these specific details. In other instances, methods, procedures and components have not been described in detail so as not to obscure the related relevant feature being described. Also, the description is not to be considered as limiting the scope of the embodiments described herein. The drawings are not necessarily to scale and the proportions of certain parts may be exaggerated to better illustrate details and features of the present disclosure.

Several definitions that apply throughout the above disclosure will now be presented. The term "coupled" is defined as connected, whether directly or indirectly through intervening components, and is not necessarily limited to physical connections. The connection can be such that the objects are permanently connected or releasably connected. The term "substantially" is defined to be essentially conforming to the particular dimension, shape or other word that substantially modifies, such that the component need not be exact. For example, "substantially cylindrical" means that the object resembles a cylinder, but can have one or more deviations from a true cylinder. The terms "comprising," "including" and "having" are used interchangeably in this disclosure. The terms "comprising," "including" and "having" mean to include, but not necessarily be limited to the things so described. The term "hot swap," "hot swapped," or "hot swappable" is defined to mean that a sensor is removed and a new calibrated sensor can be replaced such that the downtime of the therapeutic gas delivery device for the replacement sensor to reach operational readiness is less than approximately 5 minutes. For example, a gas sensor module may be hot swapped with a calibrated gas sensor module, and the downtime of the therapeutic gas delivery device is approximately 3 minutes. As used herein, "swap" can include "hot swap" or any corresponding variations.

Disclosed herein is a removable gas sensor module with a plurality of sensors for measuring at least one property of a sample gas in a therapeutic gas delivery device. The sample gas may be a sample of the therapeutic gas being delivered to a patient by the therapeutic gas delivery device. The gas sensor module is self-contained within the therapeutic gas delivery device, thereby facilitating its replacement in the field in a fashion that can be thought of as "Plug'n'Play" and/or capable of a hot swap. In some examples, the gas sensor module is self-contained within a gas sensor assembly, which is further contained within the therapeutic gas delivery device. The gas sensor module can be pre-calibrated, such that it is ready to be used upon installation in the gas sensor assembly/therapeutic gas delivery device without further calibration. The gas sensor module can be factory calibrated, and, in at least one example, can maintain calibration stability while in storage for a substantial period of time, for example over a 6-month period.

Conventionally, if a sensor fails any of the calibration tests, the sensor is replaced by a trained responsible person or service technician. For example, sensor replacement may be carried out by opening a panel on the back of the device casing, removing the failed sensor and fitting a replacement sensor. After replacing a sensor, the sample detection circuit is out of operation for a period of time as the new sensor has to be conditioned in the gas-flow, which for example sensor change for oxygen ($O_2$) and nitrogen dioxide ($NO_2$) may be about 40 minutes, while nitric oxide (NO) sensors may require about 5 hours conditioning. Once the new sensor has been conditioned, a low and then high calibration is then carried out before gas sample detection can be continued. Thus, the replacement of conventional gas sensors in a therapeutic gas delivery device is time consuming and causes an interruption in both gas sensor detection/analysis and therapeutic gas delivery to a patient that can interfere with the effective treatment of the patient.

The conventional solution to sensor drift is to carry out periodic low and high level calibration of the sensors. Low level calibration may be automatically managed and controlled by the device, but high level calibration of the sensors requires a user to disconnect the sampling line from the patient line and then attach calibration gas supplies of the appropriate gas before enabling the high calibration protocol. Again, performing the high calibration is time consuming and causes an interruption in gas sensor detection/analysis that can interfere with the effective treatment of the patient.

The gas sensor module described herein overcomes the limitations of the conventional gas sensors. The gas sensor module is pre-calibrated, self-contained, and hot swappable, such that it can be replaced in a therapeutic gas delivery device without causing an interruption in therapeutic gas delivery to a patient and only has minimal down time in gas sensor detection/analysis. This provides for continuous, effective treatment of the patient. In addition, the hot swappable feature of the self-contained gas sensor module provides for the gas sensor module to be replaced by a user without significant training. Rather than ask the user to implement a monthly high calibration of the NO and $NO_2$ sensors, the gas sensor module can simply be removed and replaced by a separate pre-calibrated gas sensor module. The first gas sensor module can then be returned to a central facility for recalibration and/or be discarded. The gas sensor module has been pre-calibrated for high calibration such that only low calibration is needed to be performed, which, in at least one example, can occur automatically upon insertion of the gas sensor module.

The gas sensor module can be utilized in an exemplary gas sensor assembly shown, for example, in FIGS. 1A and 1B. The gas sensor assembly 10 includes a gas sensor module 100 and an assembly inner housing 200 operable to removably receive the gas sensor module 100. The assembly inner housing 200 includes a module receiving portion 202 which forms a module receiving recess 204. The gas sensor module 100 is removably received in the module receiving recess 204. As such, the gas sensor module 100 is removably coupled with the assembly inner housing 200. The gas sensor assembly 10 can also include a gas analyzer unit 300 with an assembly main housing 302 operable to receive the assembly inner housing 200. In some examples, the assembly inner housing 200 is removably coupled with the assembly main housing 302. In other examples, the assembly inner housing 200 is fixedly coupled with the assembly main housing 302. The gas analyzer unit 300 is contained within a therapeutic gas delivery device 50. In at least one example, the assembly main housing 302 is coupled with and in fluid communication with the therapeutic gas delivery device 50. In some examples, the gas sensor module 100 is nested within the assembly inner housing 200, which is nested within the assembly main housing 302, such that the gas sensor module 100 is coupled with and in fluid communication with the therapeutic gas delivery device 50. In other examples, the assembly inner housing 200 and the gas analyzer unit 300 can be integrated as a single unit operable to receive the gas sensor module 100. In additional examples, the therapeutic gas delivery device 50 is operable to receive the gas sensor module 100.

The therapeutic gas delivery device 50 is operable to deliver therapeutic gas to a patient. For example, the therapeutic gas delivery device 50 can deliver therapeutic nitric oxide (NO) gas to a patient. The gas sensor module 100, the assembly inner housing 200, and the assembly main housing 302 are positioned such that gas can flow from a breathing circuit of the therapeutic gas delivery device 50, through a sample tube, through the gas analyzer unit 300, through the assembly inner housing 200, to the gas sensor module 100. In at least one example, a sample tube can be fluidly connected to a breathing circuit of the gas delivery device 50 and the gas sensor module 100 is operable to receive the sample gas from the sample tube. In at least one example, the breathing circuit of the therapeutic gas delivery device 50 includes a sample tee which is operable to receive the sample tube such that at least a portion of the gas in the breathing circuit flows through the sample tube. Additionally, in at least one example, the assembly inner housing 200 can include a port 206 which can be fluidly connected with a port 306 on the gas analyzer unit 300, which can be fluidly connected with the sample tube. The port 206 can receive the sample gas from the therapeutic gas delivery device 50, through the gas analyzer unit 300 port 304 and provide the sample gas to the gas sensor module 100.

Figure 2B:
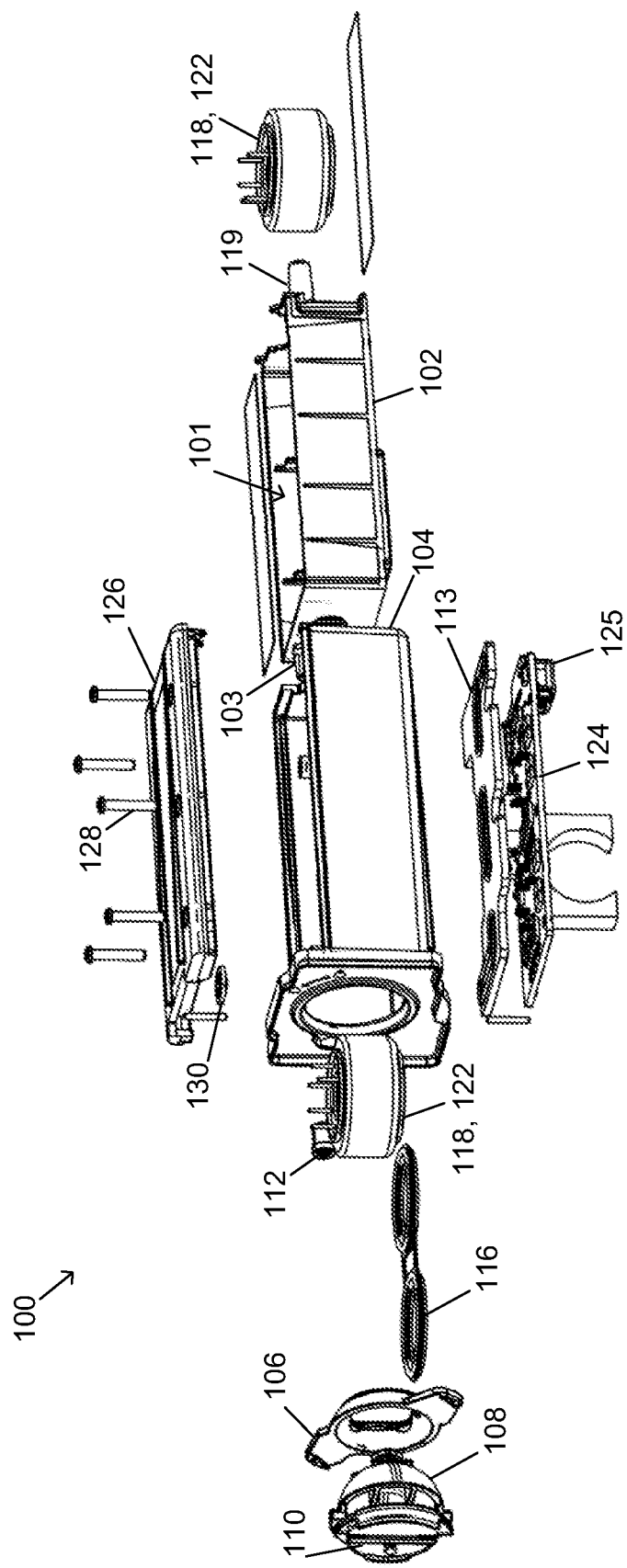
FIG. 2B is an exploded view of an exemplary gas sensor module.

FIGS. 2A and 2B illustrate exploded views of the gas sensor module 100. The gas sensor module 100 includes a sample chamber 101. The sample chamber 101 receives the sample gas from the therapeutic gas delivery device 50. The sample chamber 101 is fluidly connected with a sample inlet 119. The sample inlet 119 is fluidly connected with a therapeutic gas delivery device and is operable to receive the sample gas. In some examples, the sample inlet 119 is fluidly connected to the port 206 of the assembly inner housing 200, which is fluidly connected to the port 304 of the gas analyzer unit 300, which is fluidly connected with the sample tube in the therapeutic gas delivery device 50. In at least one example, the sample chamber 101 is operable to receive the sample gas from the therapeutic gas delivery device 50. The sample chamber 101 can include an inner housing 102. The inner housing 102 can include a vent 103 through which the sample gas can be removed from the sample chamber 101. The vent 103 can be, for example, an opening formed in the inner housing 102. In at least one example, the gas sensor module 100 includes an outer housing 104 which at least partially surrounds the inner housing 102. In some examples, the outer housing 104 can include at least one of the following: a cam element 106, a cam spindle 108, a handle 110, a handle axle 114, a vent cap 112, and/or a gasket 113. In at least some examples, the cam element 106, the cam spindle 108, the handle 110, and/or the handle axle 114 can be used to facilitate ease of insertion/removal of the gas sensor module 100 by the user via a locking/unlocking action of the vent cap 112. In some examples, the handle 110 can be a flip-up pull tab, as seen in FIG. 2B. The gasket 113 can help to prevent leaks from the pneumatic circuit, stopping sample gas from interacting with the electronics. In at least one example, the gasket 113 can be made of silicon rubber.

The gas sensor module 100 includes a gas detection unit 121 which includes a plurality of sensors 118. The sensors 118 are operable to measure at least one property of the sample gas. For example, the sensors 118 can include two or more of gas detection sensors, humidity sensors, and/or temperature sensors.

In at least one example, the gas detection unit 121 can include two or more gas detection sensors 122. In at least one example, the gas detection unit 121 can include two or more different sensors 118. As illustrated in FIGS. 2A and 2B, the gas detection unit 121 can include a humidity sensor 120 and two gas detection sensors 122. In other examples, the gas detection unit 121 can include one or more gas detection sensors 122 and a humidity sensor 120. The gas detection sensors 122 can include one or more of an NO sensor, an $NO_2$ sensor, an $O_2$ sensor, or combinations thereof. In at least one example, the gas detection sensors 122 can include an NO sensor and an $NO_2$ sensor. While FIGS. 2A and 2B illustrate two gas detection sensors 122, one, three, or more gas detection sensors 122 can be included. The property of the sample gas being measured can be one or more of a concentration of NO, a concentration of $NO_2$, a concentration of $O_2$, humidity, temperature, or a combination thereof. As illustrated in FIGS. 2A and 2B, the gas sensor module 100 includes a sensor seal 116 coupled with at least one of the sensors 118. As illustrated in FIG. 2B, the gas sensor module 100 can include a humidity sensor seal 130 operable to be coupled with a humidity sensor 120 (not shown) that can be integrated with the sensing circuit 124.

The gas sensor module 100 includes a sensing circuit 124 coupled with the sensors 118. The sensing circuit 124 is operable to detect and report the measured properties of the sample gas from the sensors 118. The sensing circuit 124 can be communicatively coupled with the gas delivery device 50. In an example, the sensing circuit 124 can be operable to report measured properties of the sample gas to a gas analyzer controller 350 in the gas analyzer unit 300. In an example, the gas analyzer controller 350 can be operable to report measured properties of the sample gas to the therapeutic gas delivery device 50. The sensing circuit 124 can be coupled with the gas analyzer controller 350 and/or the gas delivery device 50 by any suitable wired or wireless connection, for example Ethernet, Bluetooth, RFID, or fiber optic cable. In at least one example, the sensing circuit 124 and/or the gas analyzer controller 350 can be operable to store measured properties of the sample gas. The gas detection unit 121, by the sensing circuit 124, can be operable to electronically retain serial numbers, calibration data, and/or usage information of the gas sensor module 100. In another example, the gas analyzer controller 350 can be operable to electronically retain serial numbers, calibration data, and/or usage information of the gas sensor module 100. Thereby, components can continue to be tracked and traced even when the gas sensor module 100 is disconnected from the gas delivery device 50. The sensing circuit 124 can include a connector 125 operable to connect the sensing circuit 124 of the gas sensor module 100 with the gas analyzer controller 350, and thus, the gas delivery device 50. Accordingly, the gas sensor module 100 can be hot swapped, and the connector 125 is easily connected with the gas delivery device 50 without additional expertise or tools.

The gas sensor module 100 additionally includes a cover 126, which can be coupled with the outer housing 104. In at least one example, the cover 126 can be removably coupled with the outer housing 104 by fasteners 128. Fasteners 128 can be, for example, at least one of: screws, nails, nuts and bolts, hook and loop fasteners, adhesives, and/or any other suitable fasteners.

The gas sensor module 100 is self-contained within the therapeutic gas delivery device 50 and is swappable with another gas sensor module 100. The containment of all of the sensors and/or analysis elements for the gas sample provides for the ability of a hot-swap in the event of a need for recalibration, component failure, and/or contamination. For example, the gas sensor module 100 can be replaced in the event of gas sensor module 100 failure, sample line filter failure, and/or when the service period for the calibration of the gas sensor module 100 is due to expire. Additionally, the modularization of the gas sensor module 100 simplifies the future addition of sensors 118 for analytes such as $O_2$ or volatile organic compounds (VOCs) without the need to modify the overall gas delivery device 50, instead "upgrading" to a next-generation gas sensor module. A replacement gas sensor module 100 can simply be installed and the gas delivery device 50 can then immediately be put back into service. The gas sensor module 100 can be replaced with a pre-calibrated gas sensor module 100 by a responsible person in a matter of minutes without the need for special tools or equipment. For example, the replacement of the gas sensor module 100 can result in less than five minutes of down time in the measurement of at least one property of the sample gas. In at least one example, the replacement of the gas sensor module 100 can result in less than three minutes of down time in the measurement of at least one property of the sample gas.

In another example, the replacement of the gas sensor module 100 can result in no down time in delivery of therapeutic gas from the therapeutic gas delivery device 50. In this example, the delivery of therapeutic gas to the patient is uninterrupted by the replacement of the gas sensor module 100 because the gas sensor module 100 analyzes sample gas, separate from the therapeutic gas in the breathing circuit. In addition, because the gas sensor module 100 is self-contained, it does not require shutdown of the therapeutic gas delivery device 50 or any stoppage in flow of therapeutic gas to the patient. This allows for the therapeutic gas delivery device 50 to continuously deliver therapeutic gas to the patient through the breathing circuit while the gas sensor module 100 is swapped for a new pre-calibrated gas sensor module 100. In at least one example, the therapeutic gas delivery device 100 can be continuously operable when the gas sensor module 100 is replaced. Additionally, sample detection by the gas sensor module 100 can begin approximately five minutes after installation, following completion of a low calibration protocol. In at least one example, the low calibration protocol can start automatically upon installation of a new gas sensor module 100. The hot-swap ability of the gas sensor module 100 has a significant, positive impact on user experience and device downtime. The gas sensor module 100 being pre-calibrated, or calibrated prior to installation, eliminates the need for onsite high calibration of NO sensors and enables fast and simple replacement of a failed or expired gas sensor module, allowing for off-site re-calibration and repair if applicable.

The gas sensor module 100 can be utilized, or in-use, and maintain calibration stability for at least one month. In at least one example, the in-use calibration stability period for the gas sensor module 100 can be extended from the conventional one month to approximately three months. In at least one example, the gas sensor module 100 can have a shelf-life calibration stability period (for example, stability when not installed in a gas delivery device 50) of at least 1 month, alternately at least 3 months, alternately at least 6 months, or alternately at least 1 year. In some examples, the shelf-life of the gas sensor module 100 may be extended by including a battery 132 or other voltage source to provide an electrical potential across the sensors during storage to maintain the calibration. In at least one example, the gas sensor module 100 can include an expiration date. A user can be provided with gas sensor module replacement reminders/alarms via, for example, a graphic user interface and/or an app and/or program associated with the therapeutic gas delivery device.

Figure 2C:
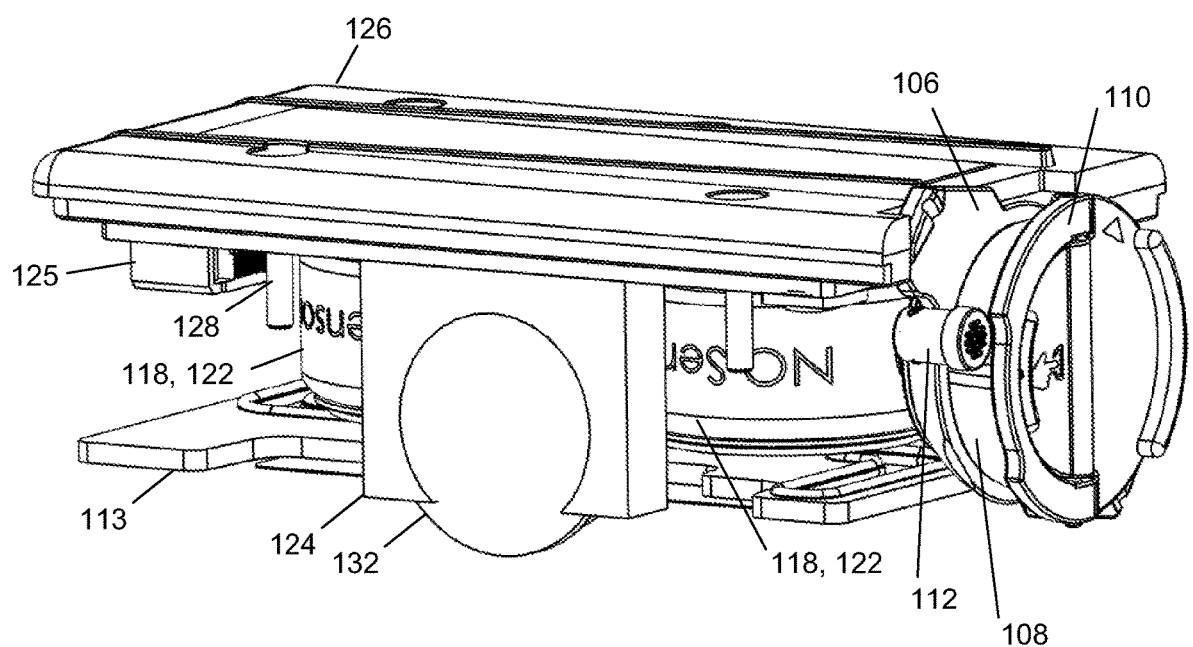
FIG. 2C is an assembled view of the gas sensor module of FIG. 2B with the outer housing and inner housing removed.
Figure 4:
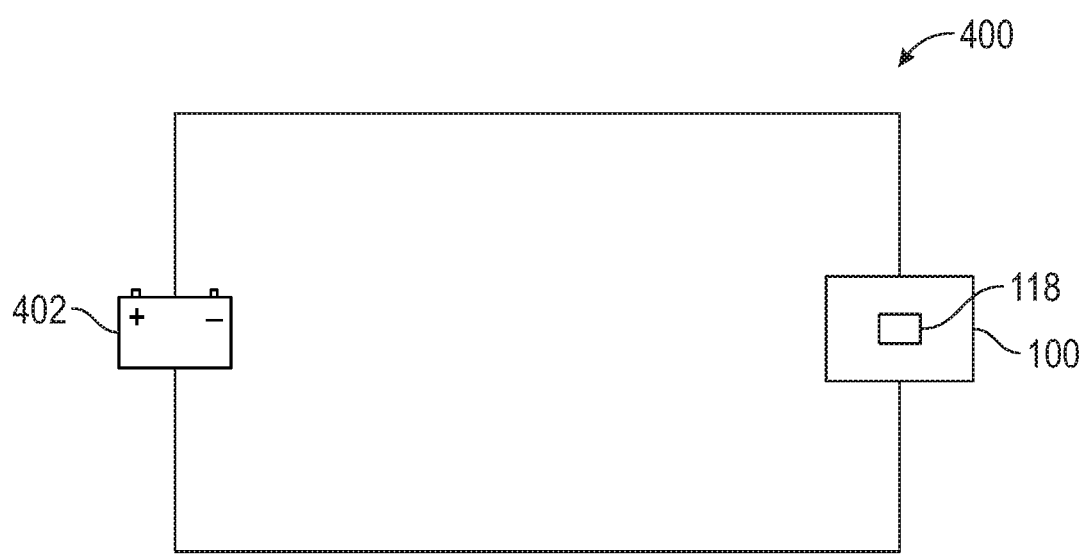
FIG. 4 is a schematic diagram of an apparatus including a voltage source electrically coupled with a gas sensor module to maintain calibration stability of the gas sensor module.

In at least one example, as illustrated in FIG. 4, the gas sensor module 100 can include and/or be electrically connected to an apparatus 400 which includes a voltage source 402 that may be used in conjunction with an ultra-low power consumption setting to ensure the sensors 118 retain calibration stability for a predetermined period, for example, up to 6 months. The plurality of sensors 118 in the gas sensor module 100 can be pre-calibrated, and with the apparatus 400, an electrical potential can be provided across the sensors 118 to maintain the calibration of the sensors 118. For example, the voltage source 402 may provide an electrical potential across the plurality of sensors 118 of the gas sensor module 100 at predetermined times to maintain calibration stability of the sensors 118 when the gas sensor module 100 is in a non-installed configuration. As such, the end-user may order multiple gas sensor modules 100, keeping them in storage until they are required to replace in-use gas sensor modules 100 when recalibration and/or replacement is due. In at least one example, the voltage source 402 can be a battery or a power transformer. In at least one example, the voltage source 402 can be internal to the gas sensor module 100, as seen in FIG. 2C. In other examples, the voltage source 402 can be external to the gas sensor module 100. The voltage source 402 can cease to provide electrical potential across the sensors 118 when the gas sensor module 100 is installed within the therapeutic gas delivery device 50. In at least one example, the apparatus 400 and the voltage source 402 can be removable from the gas sensor module prior to installation in the therapeutic gas delivery device 50. In another example, the voltage source 402 can remain connected to the gas sensor module 100 after installation but no longer provide an electrical potential across the sensors 118, 122 of the gas sensor module 100. In at least one example, as illustrated in FIG. 2C, the battery 132 can directly connect with the sensing circuit 124 such that a separate apparatus 400 is not needed to connect the battery 132 to the gas sensor module 100.

The implementation of pre-calibration and/or off-site calibration provides for calibration accuracy. For example, the conventional, single-point high calibration protocol assumes a single linear function across the range of administered NO concentrations. While sufficient to address current requirements for a +/−20% calibration accuracy, this could be improved upon significantly by employing a multi-point calibration protocol, something that is not compatible with a user-run calibration but which can be carried out automatically in a factory calibration scenario. With such an approach, calibration functions for multiple sub-ranges of NO concentration may be generated and stored for implementation (for example, in the form of a simple lookup table in device memory). The gas sensor module 100 can then determine the appropriate calibration function to use when measuring gas delivery based on, for example, the set dose and the range in which it sits. This is particularly important in pediatric or other low concentration applications for NO administration, where many calibration gases are supplied at a set concentration of 45 ppm, often more than twice the administered NO concentration. This would also address an issue experienced with certain users, who are uncomfortable with the display of a concentration that may be up to 20% less/greater than the set dose.

Furthermore, an off-site (for example factory) calibration and/or pre-calibration can utilize a calibration manifold 356 (shown in FIGS. 3A and 3B) that can control at least one of temperature, relative humidity, and pressure, facilitating the generation of calibration functions that not only provide a more accurate measurement of gas, such as NO, in specific sub-ranges but also enable compensation for different temperatures, pressures, and relative humidity values.

Additionally, an off-site calibration and/or pre-calibration can facilitate precise measurement of the gas, such as NO, concentration used in the calibration gas mixture. Rather than use calibrated gas cylinders that have been prepared in batches for distribution to end-users, calibration gas can be precisely quantified in terms of gas concentration.

Figure 3A:
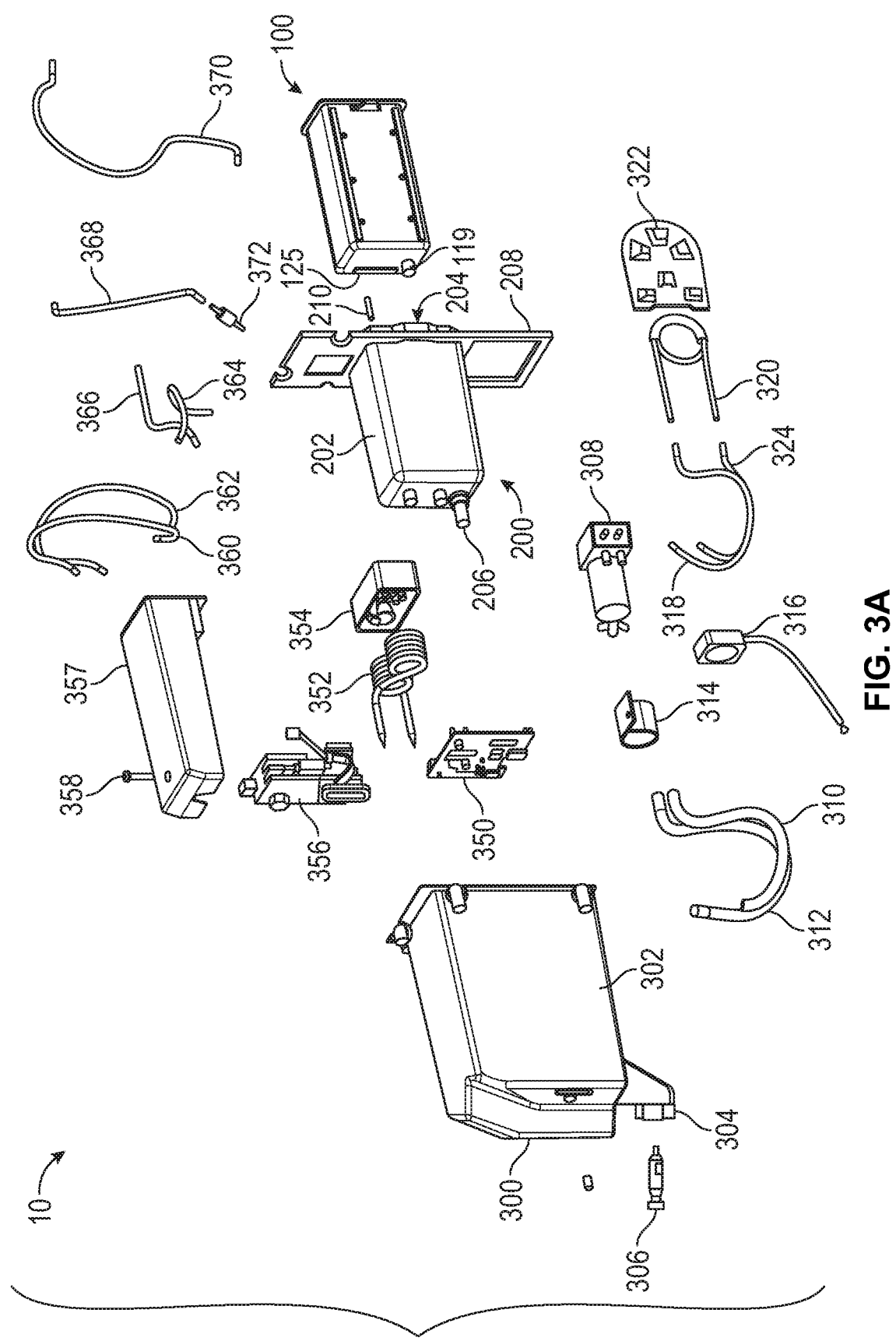
FIG. 3A is a detailed, exploded view of an exemplary gas sensor assembly.
Figure 3B:
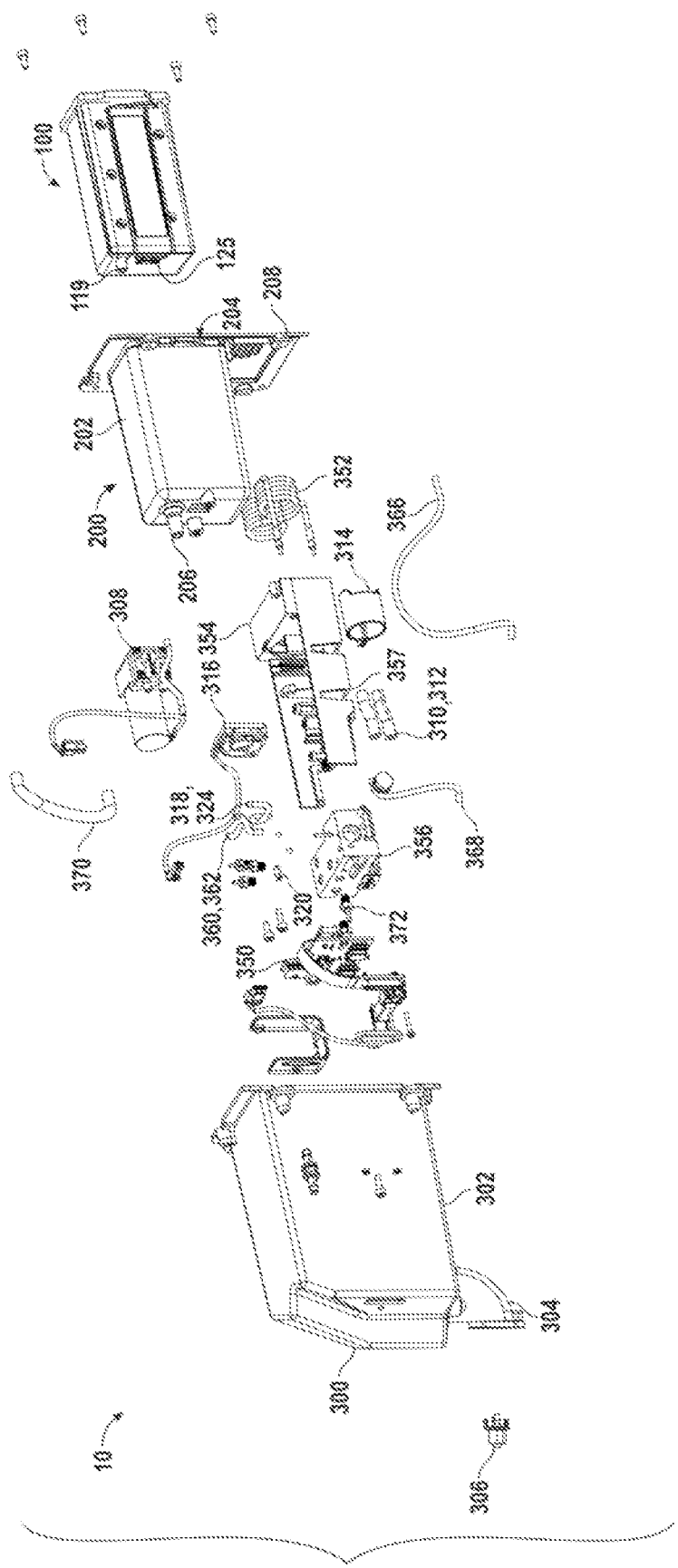
FIG. 3B is a detailed, exploded view of an exemplary gas sensor assembly.

FIGS. 3A and 3B illustrate a detailed exploded view of a gas sensor assembly 10. As discussed above, the gas sensor assembly 10 includes the gas sensor module 100 which is removably received in the assembly inner housing 200. The gas sensor module 100 can be removably coupled with the assembly inner housing 200 by one or more fasteners such as, for example, screws, clips, rotatable abutments, or any other suitable fastener such that the gas sensor module 100 can be removed from the assembly inner housing 200 without special tools or expertise. The assembly inner housing 200 can be received in and/or coupled with the assembly main housing 302, which is within or in fluid communication with the therapeutic gas delivery device. In an example, the assembly inner housing 200 and the assembly main housing 302 remain fixed within the therapeutic gas delivery device, while the gas sensor module 100 is removably replaced as needed.

A sample gas is taken from the therapeutic gas delivery device and passed to the gas sensor module 100 through the gas sensor assembly 10 such that the gas sensor module 100 can detect and report at least one property of the sample gas. The sample gas can enter the assembly main housing through port 304. In an example, a two stage filter luer interface 306 can be connected to the port 304, external to the assembly main housing 302. The port 304 can be fluidly connected to a pump 308 inside the assembly main housing 302. The pump 308 is operable to pump the sample gas through the gas sensor module 100. The pump 308 can retrieve the sample gas from the gas delivery device, for example, through the port 304 and a pump feeder tube 310. The pump feeder tube 310 can be coupled with the pump 308 using a fastener 314, such as a clip. The pump 308 includes a fan 316 which is operable to be rotated to promote flow of the sample gas. In at least one example, the sample gas can then be received in a restrictor feed tube 318, passed through a restrictor 320 which is received in a restrictor housing 322, and passed through a restrictor return tube 324. The restrictor 320 can be operable to restrict gas flow by creating a pressure differential. In at least some examples, the restrictor 320 can be incorporated into the calibration manifold 356. In other examples, as seen in FIG. 3B, the gas analyzer unit 300 may not include the restrictor feed tube, restrictor, restrictor housing, or restrictor return tube. In this example, the calibration manifold 356 can incorporate the function of the restrictor 230 by including a restrictor aperture to restrict sample gas flow to create the pressure differential, as seen in FIG. 3B.

The restrictor 320 and/or calibration manifold 356 can be utilized to control the speed and/or quantity of the sample gas received by the gas sensor module 100. The sample gas can then pass through the pump 308 and out the pump delivery tube 312.

The gas sensor assembly 10 can include a sample tube 352 fluidly connected to the gas delivery device 50 and the gas sensor module 100 operable to receive the sample gas. For example, the sample tube 352 can be fluidly connected to the pump delivery tube 312. In at least one example, at least a portion of the sample tube 352 can be a Nafion tube. As illustrated in FIGS. 3A and 3B, the gas sensor assembly 10 can additionally include a humidity component 354 and a calibration manifold 356. The humidity component 352, the Nafion tube portion of the sample tube 352, the calibration manifold 356, any other suitable components for example to control the temperature and/or pressure, or any combination thereof can control at least one of temperature, relative humidity, and pressure, facilitating the generation of calibration functions that not only provide a more accurate measurement of gas, such as NO, in specific sub-ranges but also enable compensation for different temperatures, pressures, and/or relative humidity values. For example, the humidity component 352, the Nafion tube portion of the sample tube 352, and/or the calibration manifold 356 can lower the humidity of the gas sample to increase the calibration stability of the gas sensor module 100. A gas analyzer subframe 357 can be included to house at least a portion of the humidity component 352, the Nafion tube portion of the sample tube 352, and/or the calibration manifold 356. One or more fasteners 358 can retain at least one of the humidity component 352, the Nafion tube portion of the sample tube 352, and/or the calibration manifold 356 within the gas analyzer subframe 357. The fasteners 358 can be, for example, screws, adhesives, and/or nuts and bolts.

The gas sensor assembly 10 additionally can include a high differential link tube 360 and a low differential link tube 362. In at least one example, the gas sensor assembly 10 can include an ambient air pressure link tube 364 which is fluidly connected with external atmosphere or ambient air. To provide ambient air, the gas sensor assembly 10 can include an ambient air inlet tube 368 which is fluidly connected with exterior of the gas sensor assembly 10 to provide ambient air. A filter 372 is coupled with an end of the ambient air inlet tube 368 opposite the end connected with the exterior of the gas sensor assembly 10. The filter 372 can filter the ambient air to prevent particles or other substances which may affect the gas sensor module 100 from determining accurate measurements of the sample gas. A connector tube 366 can be included to fluidly connect the Nafion tube portion of the sample tube 352 with the calibration manifold 356. Additionally, in at least one example, a filter tube 370 can be fluidly connected with the filter 372 to provide a passage of the ambient air to the Nafion tube portion of the sample tube 352.

The sample gas is received through the port 206 of the assembly inner housing 200. The port 206 is fluidly connected with the sample inlet 119 of the gas sensor module 100, and the sample gas is received within the sample chamber 101 of the gas sensor module 100.

Also provided herein is a method for providing a gas sensor module for use in a therapeutic gas delivery device. In some examples, the method may include calibrating the plurality of sensors in the gas sensor module, and providing electrical potential across the plurality of sensors to maintain the calibration of the plurality of sensors. The calibration of the plurality of sensors can be maintained for at least 1 month, at least 3 months, at least 6 months, or at least 1 year. The electrical potential may be provided by an apparatus with a voltage source, such as a battery. In some examples, the method may further include removing the apparatus/voltage source prior to or simultaneously with the installation of the gas sensor module in the therapeutic gas delivery device. The gas sensor module can be installed within the assembly inner housing and assembly outer housing in the therapeutic gas delivery device. In some examples, the installation of the gas sensor module results in less than 5 minutes of down time in the measurement of at least one property of a sample gas from the therapeutic gas delivery device. In other examples, the installation of the gas sensor module results in no down time in the delivery of therapeutic gas to a patient.

The disclosures shown and described above are only examples. Even though numerous characteristics and advantages of the present technology have been set forth in the foregoing description, together with details of the structure and function of the present disclosure, the disclosure is illustrative only, and changes may be made in the detail, especially in matters of shape, size and arrangement of the parts within the principles of the present disclosure to the full extent indicated by the broad general meaning of the terms used in the attached claims. It will therefore be appreciated that the examples described above may be modified within the scope of the appended claims.

Numerous examples are provided herein to enhance the understanding of the present disclosure. A specific set of statements are provided as follows.

Statement 1: A removable gas sensor module for a therapeutic gas delivery device, the gas sensor module comprising: a sample chamber operable to receive a sample gas from the therapeutic gas delivery device; and a gas detection unit comprising a plurality of sensors operable to measure at least one property of the sample gas, wherein the plurality of sensors include two or more of a gas detection sensor, a humidity sensor, a temperature sensor, or a combination thereof, wherein the gas sensor module is self-contained within the therapeutic gas delivery device and swappable with another gas sensor module.

Statement 2: The gas sensor module of Statement 1, wherein replacement of the gas sensor module results in less than 5 minutes of down time of the measurement of at least one property of the sample gas.

Statement 3: The gas sensor module of Statement 1, wherein replacement of the gas sensor module results in no down time in delivery of therapeutic gas from the therapeutic gas delivery device.

Statement 4: The gas sensor module of Statement 1, wherein the gas detection sensor is one or more of an NO sensor, an $NO_2$ sensor, an $O_2$ sensor, or combinations thereof.

Statement 5: The gas sensor module of Statement 1, wherein the gas detection unit comprises at least two gas detection sensors.

Statement 6: The gas sensor module of Statement 4, wherein the gas detection unit comprises an NO sensor and an $NO_2$ sensor.

Statement 7: The gas sensor module of Statement 1, wherein the gas detection unit comprises two or more different sensors.

Statement 8: The gas sensor module of Statement 6, wherein the gas detection unit comprises one or more gas detection sensors and a humidity sensor.

Statement 9: The gas sensor module of Statement 1, wherein the at least one property of the sample gas is one or more of a concentration of NO, a concentration of $NO_2$, a concentration of $O_2$, humidity, temperature, or a combination thereof.

Statement 10: The gas sensor module of Statement 1 further comprising a sensing circuit operable to detect and report the at least one property of the sample gas to a gas analyzer controller in the therapeutic gas delivery device.

Statement 11: The gas sensor module of Statement 1, wherein the therapeutic gas delivery device is continuously operable when the gas sensor module is replaced.

Statement 12: The gas sensor module of Statement 1, wherein the sample chamber comprises an inner housing and an outer housing.

Statement 13: The gas sensor module of Statement 1, wherein the gas detection unit is operable to electronically store or send to the therapeutic gas delivery device serial numbers, calibration data, and/or usage information of the gas sensor module.

Statement 14: The gas sensor module of Statement 1, wherein the gas sensor module is pre-calibrated and shelf stable for at least 1 month.

Statement 15: The gas sensor module of Statement 13, wherein the gas sensor module is shelf stable for at least 3 months.

Statement 16: A gas sensor assembly comprising: the gas sensor module of any one of Statements 1-15; an assembly inner housing operable to removably receive the gas sensor module; and a gas analyzer unit comprising: a sample tube fluidly connected to the gas delivery device and the gas sensor module operable to receive the sample gas; and a pump connected to the gas sensor module through the sample tube, wherein the pump is operable to pump the sample gas through the gas sensor module.

Statement 17: The gas sensor assembly of Statement 16, wherein the gas analyzer unit further comprises a gas analyzer controller.

Statement 18: The gas sensor assembly of Statement 16, wherein the gas analyzer unit further comprises an assembly main housing operable to receive the assembly inner housing, wherein the assembly main housing is within the therapeutic gas delivery device.

Statement 19: The gas sensor assembly of Statement 16, wherein at least a portion of the sample tube is a Nafion tube.

Statement 20: An apparatus comprising: a voltage source; and the gas sensor module of any one of Statements 1-15, wherein the voltage source provides an electrical potential across the plurality of sensors in the gas detection unit to maintain calibration of the plurality of sensors when the gas sensor module is in a non-installed configuration.

Statement 21: The apparatus of Statement 20, wherein the voltage source is a battery or a power transformer.

Statement 22: The apparatus of Statement 20, wherein the voltage source ceases to provide electrical potential across the plurality of sensors when the gas sensor module is installed within the therapeutic gas delivery device.

Statement 23: The apparatus of Statement 20, wherein the current source is internal to the gas sensor module.

Statement 24: A method for providing a gas sensor module comprising: calibrating the plurality of sensors in the gas sensor module of any one of Statements 1-15; and providing electrical potential across the plurality of sensors to maintain the calibration of the plurality of sensors.

What is claimed is:

1. A removable gas sensor module for a therapeutic gas delivery device, the gas sensor module comprising:
    a sample chamber operable to receive a sample gas from the therapeutic gas delivery device; and
    a gas detection unit comprising a plurality of sensors operable to measure at least one property of the sample gas, wherein the plurality of sensors include two or more of a gas detection sensor, a humidity sensor, a temperature sensor, or a combination thereof,
    wherein the gas sensor module is self-contained within the therapeutic gas delivery device and swappable with another gas sensor module,
    wherein the plurality of sensors is pre-calibrated and shelf stable in a non-installed configuration for at least 1 month,
    wherein the plurality of sensors includes an NO sensor and an $NO_2$ sensor,
    wherein the plurality of sensors is operable to receive an electrical potential from a voltage source when the gas sensor module is not installed in the therapeutic gas delivery device, and
    wherein the electrical potential maintains the pre-calibration of the plurality of sensors when the gas sensor module is not installed in the therapeutic gas delivery device.

2. The gas sensor module of claim 1, wherein replacement of the gas sensor module results in less than 5 minutes of down time of the measurement of at least one property of the sample gas.

3. The gas sensor module of claim 1, wherein replacement of the gas sensor module results in no down time in delivery of therapeutic gas from the therapeutic gas delivery device.

4. The gas sensor module of claim 1, wherein the gas detection sensor is one or more of an NO sensor, an $NO_2$ sensor, an $O_2$ sensor, or combinations thereof.

5. The gas sensor module of claim 1, wherein the gas detection unit comprises at least two gas detection sensors.

6. The gas sensor module of claim 1, wherein the gas detection unit comprises two or more different sensors.

7. The gas sensor module of claim 6, wherein the gas detection unit comprises one or more gas detection sensors and a humidity sensor.

8. The gas sensor module of claim 1, wherein the at least one property of the sample gas is one or more of a concentration of NO, a concentration of $NO_2$, a concentration of $O_2$, humidity, temperature, or a combination thereof.

9. The gas sensor module of claim 1 further comprising a sensing circuit operable to detect and report the at least one property of the sample gas to a gas analyzer controller in the therapeutic gas delivery device.

10. The gas sensor module of claim 1, wherein the therapeutic gas delivery device is continuously operable when the gas sensor module is replaced.

11. The gas sensor module of claim 1, wherein the sample chamber comprises an inner housing and an outer housing.

12. The gas sensor module of claim 1, wherein the gas detection unit is operable to electronically store or send to the therapeutic gas delivery device serial numbers, calibration data, and/or usage information of the gas sensor module.

13. The gas sensor module of claim 1, wherein the gas sensor module is shelf stable for at least 3 months.

14. A gas sensor assembly comprising:
    the gas sensor module of claim 1;
    an assembly inner housing operable to removably receive the gas sensor module; and
    a gas analyzer unit comprising:
        a sample tube fluidly connected to the gas delivery device and the gas sensor module operable to receive the sample gas; and
        a pump connected to the gas sensor module through the sample tube, wherein the pump is operable to pump the sample gas through the gas sensor module.

15. The gas sensor assembly of claim 14, wherein the gas analyzer unit further comprises a gas analyzer controller.

16. The gas sensor assembly of claim 14, wherein the gas analyzer unit further comprises an assembly main housing operable to receive the assembly inner housing, wherein the assembly main housing is within the therapeutic gas delivery device.

17. The gas sensor assembly of claim 14, wherein at least a portion of the sample tube is a Nafion tube.

18. An apparatus comprising:
   a voltage source; and
   a gas sensor module comprising:
      a sample chamber operable to receive a sample gas from a therapeutic gas delivery device; and
      a gas detection unit comprising a plurality of sensors operable to measure at least one property of the sample gas, wherein the plurality of sensors include two or more of a gas detection sensor, a humidity sensor, a temperature sensor, or a combination thereof,
   wherein the gas sensor module is self-contained within the therapeutic gas delivery device and swappable with another gas sensor module,
   wherein the plurality of sensors is pre-calibrated and stable in a non-installed configuration for at least 1 month,
   wherein the plurality of sensors includes an NO sensor and an $NO_2$ sensor,
   wherein the voltage source provides an electrical potential across the plurality of sensors in the gas detection unit to maintain the pre-calibration of the plurality of sensors when the gas sensor module is in the non-installed configuration.

19. The apparatus of claim 18, wherein the voltage source is a battery or a power transformer.

20. The apparatus of claim 18, wherein the voltage source ceases to provide the electrical potential across the plurality of sensors when the gas sensor module is installed within the therapeutic gas delivery device.

21. The apparatus of claim 18, wherein the voltage source is internal to the gas sensor module.

22. A method for providing a gas sensor module comprising:
   calibrating the plurality of sensors in the gas sensor module of claim 1; and
   providing electrical potential across the plurality of sensors to maintain the calibration of the plurality of sensors.

* * * * *